United States Patent [19]
Frommer et al.

[11] Patent Number: 5,981,181
[45] Date of Patent: Nov. 9, 1999

[54] DNA SEQUENCES WITH OLIGOSACCHARIDE TRANSPORTER, PLASMIDS BACTERIA AND PLANTS CONTAINING A TRANSPORTER AS WELL AS A PROCESS FOR THE PREPARATION AND TRANSFORMATION OF YEAST STRAINS FOR IDENTIFICATION OF THE TRANSPORTER

[75] Inventors: Wolf-Bernd Frommer; Jorg Riesmeier, both of Berlin, Germany

[73] Assignee: Hoechst Schering AgrEvo GmbH, Berlin, Germany

[21] Appl. No.: 08/786,555

[22] Filed: Jan. 21, 1997

Related U.S. Application Data

[62] Division of application No. 08/356,340, Dec. 21, 1994, Pat. No. 5,608,146.

[30] Foreign Application Priority Data

Jun. 24, 1992 [DE] Germany .................. 42 20 759

[51] Int. Cl.$^6$ .................. C12Q 1/68; C07K 5/00; C07H 21/04; A01H 5/00
[52] U.S. Cl. .................. 435/6; 435/69.1; 435/91.1; 435/252.3; 435/254.2; 435/410; 435/417; 435/419; 530/350; 536/23.2; 536/23.6; 800/205
[58] Field of Search .................. 536/23.2, 23.6; 435/69.1, 6, 70.1, 91.1, 172.2, 410, 417, 419, 252.3, 254.1; 800/205; 530/350

[56] References Cited

U.S. PATENT DOCUMENTS 5,585,479  12/1996  Hoke et al. .................. 536/24.5

OTHER PUBLICATIONS

Uhlmann et al., Antisense oligonucleotides: a new therapeutic principle, Chemical Reviews, vol. 90(4), pp. 543–584, Jun. 1990.

Plant Physiology, vol. 89, No. 4, Apr. 1989, Rockville, MD, U.S.A., p. 155 , Ripp, K.G., et al. "cDNA Cloning and the Deduced Amino Acid Sequence of a Plasma Membrane Protein Implicated in Sucrose Transport".

Plant Physiology, vol. 99, No. 1, May 1992, Rockville, MD, U.S.A., p. 84, Overvoorde, P. J., et al. Biochemical and Molecular Characterization of the Soybean Membrane 62kD Sucrose Binding and Its Possible Role in Sucrose Transport.

Biochem. Biophys. ACTA, vol. 1103, No. 2, 1992, pp. 259–267, Li, Z–S et al., "The Sucrose Carrier of the Plant Plasmalemma: III. Partial Purification and Reconstitution of Active Sucrose Transport in Liposomes".

EMBO Journal, vol. 9, No. 10, Oct. 1990 EYNSHAM, Oxford GB, pp. 3045–3050, Sauer, N. et al., "Primary Structure, Genomic Organization and Heterologous Expression of a Glucose Transporter from Arabidopsis Thaliana".

The Plant Cell, vol. 5, No. 8 Aug. 1993, pp. 823–830, Raikhel, N.V. et al., The Wide World of Plant Molecular Genetics'p. 825, Col. 2 & NATO Advanced Study Institute Course, May 10–19, 1993.

Palnt Physiology, vol. 99, No. 1 May 1992, Rockville, MD, U.S.A., p. 9, Kossman, J. et al., "Functional Analysis of the Plastidic Fructose–1,6–biphosphatase and the Triose Phosphate translocator from potato".

EMBO Journal, vol. 9, No. 10, 1990, EYNSHAM, Oxford GB pp. 3033–3044, Von Schaewen, A., et al. "Expression of a Yeast–Derived Invertase in the Cell Wall of Tabacco and Arabidopsis Plants Leads to Accumulation of Carbohydrate and Inhibition of Photosynthesis and Strongly Influences Growth and Phenotype of Transgene Tobacco Plants".

Plant Physiology, vol. 95, 1991, Rockville, MD, U.S.A., pp. 420–425, Dickinson, C. D. et al., "Slow–Growth Phenotype of Transgenic Tomato Expressing Apoplastic Invertase".

Gene, vol. 95, 1990, Amsterdam NL, pp. 17–23, Blatch, G.L. et al., "Nucleotide Sequence and Analysis of the Vibrio Alginolyticus Sucrose Uptake–Encoding Region".

Recent Advances in Phloem Transport and Assimilate Compartmentation, Fourth International Conference, Aug. 19–24, 1990, 1991, pp. 154–166, Delrot, S., et al., "Use of Plasma Membrane Vesicles From Sugar Beet Leaves for the Study of Sucrose Transport and of Sucrose Transporters".

EMBO Journal, vol. 11, No. 13, Dec. 1992, Eynsham, Oxford GB, pp. 4705–4713, Riesmeier, J.W. et al. "Isolation and Characterization of a Sucrose Carrier cDNA from Spinach by Functional Expression in Yeast".

*Primary Examiner*—George C. Elliott
*Assistant Examiner*—Andrew Wang
*Attorney, Agent, or Firm*—Frommer Lawrence & Haug LLP

[57] ABSTRACT

There are described DNA sequences, that contain the coding region of an oligosaccharide transporter, whose introduction in a plant genome modifies the formation and transfer of storage materials in transgenic plants, plasmids, bacteria and plants containing these DNA sequences, a process for the preparation and transformation of yeast strains, that makes possible the identification of the DNA sequences of the plant oligosaccharide transporter of the invention, as well as the use of DNA sequences of the invention.

18 Claims, 6 Drawing Sheets

SEQUENCE LISTING

<160> NUMBER OF SEQ ID NOS: 11

<210> SEQ ID NO 1
<211> LENGTH: 1969
<212> TYPE: DNA
<213> ORGANISM: Spinacia oleracea

<400> SEQUENCE: 1

```
aaaaacacac acccaaaaaa aaaacactac gactatttca aaaaaaacat tgttactaga      60
aatcttatta tggcaggaag aaatataaaa aatggtgaaa ataacaagat tgcgggttct     120
tctcttcact tagagaagaa cccaacaact cccccgagg ccgaggctac cttaaagaag     180
ctcggcctcg tggcttcagt agcggccggg gttcagttcg ggtgggcttt acagctctcc     240
ctactgaccc cgtacgtcca actactgggc attccccaca cttgggccgc ctacatctgg     300
ttgtgcggcc caatctcggg gatgattgtc cagccattgg tcgggtacta tagtgaccgg     360
tgcacctccc gcttcggccg acgtcgcccc ttcattgcag caggggcggc tctagtggcc     420
gtagcggtgg ggctaatcgg attcgccgcc gatatcggcg cagcgtcggg tgatccaacg     480
ggaaacgtgg caaaccccg ggccatcgcg gtgtttgtgg tcgggttttg gatcctcgac     540
gtggctaaca cacccctgca aggcccatgc agggcgttgt tagcagacat ggccgccggg     600
tcgcaaacca aaaccggta cgctaacgcc ttcttctcct tcttcatggc gttaggaaac     660
atcggagggt acgccgccgg ttcatacagc cgcctctaca cggtgttccc ctttaccaaa     720
accgccgcct gcgacgtcta ctgcgccaat ctaaaatcct gcttcttcat ctccatcaca     780
ctcctaatcg tcctcacaat cctagcactt tccgtcgtaa aagagcgtca aatcacaatc     840
gacgaaatcc aagaagaaga agacttaaaa aacagaaaca atagcagcgg ttgtgcaaga     900
ctaccgttct tcggacaatt aataggcgct ctcaaagatc taccaaaacc aatgctaatc     960
ctattactag taacagccct aaattggatc gcatggtttc cattcttgtt gttcgatact    1020
gattggatgg gtaaagaagt gtacggtggt acagtcggag aaggtaaatt gtacgaccaa    1080
ggagttcatg ccggtgcctt aggtctgatg attaactccg ttgtcttagg tgttatgtcg    1140
ttgagtattg aaggtttggc tcgtatggta ggcggtgcta aaaggttatg gggaattgtc    1200
aatattattc ttgctgtttg tttagctatg acggtgttag ttactaagtc cgccgaacac    1260
ttccgtgata gccaccatat tatgggctcc gccgtccctc cgccgccgcc tgctggtgtt    1320
aagggtggcg ctttggctat ctttgccgtt cttggtatcc ctcttgcgat cactttcagt    1380
attcctttgg ccttggcgtc aatcttttca gcatcttccg gttcaggaca aggtctttct    1440
ctaggagttc tcaacctcgc catcgttgta ccccagatgt ttgtgtcggt aacaagtggg    1500
ccatgggatg caatgtttgg tggaggaaat ttgccagcat tcgtggtggg agctgtagca    1560
gcaacagcca gtgcagttct ttcatttaca ttgttgcctt ctccaccccc tgaagctaaa    1620
attggtgggt ccatgggtgg tcattaagaa atttaatact actccgtaca atttaaaccc    1680
aaattaaaaa tgaaaatgaa aatttttaac ccatgttcgt tacgttgtaa ttagagagaa    1740
aaatgatata ttgaacgaag ccgttaattt atgctccgtt catcttgtaa ttcttttct    1800
ctctgctttt tttttttttt tttaacgcga cgtgtttttg agataaggaa gggctagatc    1860
gaggatgggg gaattggcaa gaaattgctc gggtataaat atttatccct ctttgtaatt    1920
ttcagtaaca tttaatagcc agaaatcaaa aagtcaagaa aaatcgaaa                1969
```

<210> SEQ ID NO 2

```
<211> LENGTH: 525
<212> TYPE: PRT
<213> ORGANISM: Spinacia oleracea

<400> SEQUENCE: 2

Met Ala Gly Arg Asn Ile Lys Asn Gly Glu Asn Asn Lys Ile Ala Gly
 1               5                  10                  15

Ser Ser Leu His Leu Glu Lys Asn Pro Thr Thr Pro Glu Ala Glu
            20                  25                  30

Ala Thr Leu Lys Lys Leu Gly Leu Val Ala Ser Val Ala Ala Gly Val
            35                  40                  45

Gln Phe Gly Trp Ala Leu Gln Leu Ser Leu Leu Thr Pro Tyr Val Gln
 50                  55                  60

Leu Leu Gly Ile Pro His Thr Trp Ala Ala Tyr Ile Trp Leu Cys Gly
 65                  70                  75                  80

Pro Ile Ser Gly Met Ile Val Gln Pro Leu Val Gly Tyr Tyr Ser Asp
                85                  90                  95

Arg Cys Thr Ser Arg Phe Gly Arg Arg Pro Phe Ile Ala Ala Gly
                100                 105                 110

Ala Ala Leu Val Ala Val Ala Val Gly Leu Ile Gly Phe Ala Ala Asp
            115                 120                 125

Ile Gly Ala Ala Ser Gly Asp Pro Thr Gly Asn Val Ala Lys Pro Arg
130                 135                 140

Ala Ile Ala Val Phe Val Val Gly Phe Trp Ile Leu Asp Val Ala Asn
145                 150                 155                 160

Asn Thr Leu Gln Gly Pro Cys Arg Ala Leu Leu Ala Asp Met Ala Ala
                165                 170                 175

Gly Ser Gln Thr Lys Thr Arg Tyr Ala Asn Ala Phe Phe Ser Phe Phe
            180                 185                 190

Met Ala Leu Gly Asn Ile Gly Gly Tyr Ala Ala Gly Ser Tyr Ser Arg
        195                 200                 205

Leu Tyr Thr Val Phe Pro Phe Thr Lys Thr Ala Ala Cys Asp Val Tyr
210                 215                 220

Cys Ala Asn Leu Lys Ser Cys Phe Phe Ile Ser Ile Thr Leu Leu Ile
225                 230                 235                 240

Val Leu Thr Ile Leu Ala Leu Ser Val Val Lys Glu Arg Gln Ile Thr
                245                 250                 255

Ile Asp Glu Ile Gln Glu Glu Glu Asp Leu Lys Asn Arg Asn Asn Ser
            260                 265                 270

Ser Gly Cys Ala Arg Leu Pro Phe Phe Gly Gln Leu Ile Gly Ala Leu
        275                 280                 285

Lys Asp Leu Pro Lys Pro Met Leu Ile Leu Leu Val Thr Ala Leu
290                 295                 300

Asn Trp Ile Ala Trp Phe Pro Phe Leu Leu Phe Asp Thr Asp Trp Met
305                 310                 315                 320

Gly Lys Glu Val Tyr Gly Gly Thr Val Gly Glu Gly Lys Leu Tyr Asp
                325                 330                 335

Gln Gly Val His Ala Gly Ala Leu Gly Leu Met Ile Asn Ser Val Val
            340                 345                 350

Leu Gly Val Met Ser Leu Ser Ile Glu Gly Leu Ala Arg Met Val Gly
        355                 360                 365

Gly Ala Lys Arg Leu Trp Gly Ile Val Asn Ile Ile Leu Ala Val Cys
370                 375                 380

Leu Ala Met Thr Val Leu Val Thr Lys Ser Ala Glu His Phe Arg Asp
385                 390                 395                 400
```

```
Ser His His Ile Met Gly Ser Ala Val Pro Pro Pro Ala Gly
            405                 410             415

Val Lys Gly Gly Ala Leu Ala Ile Phe Ala Val Leu Gly Ile Pro Leu
        420                 425             430

Ala Ile Thr Phe Ser Ile Pro Leu Ala Leu Ala Ser Ile Phe Ser Ala
        435             440             445

Ser Ser Gly Ser Gly Gln Gly Leu Ser Leu Gly Val Leu Asn Leu Ala
    450             455             460

Ile Val Val Pro Gln Met Phe Val Ser Val Thr Ser Gly Pro Trp Asp
465             470             475             480

Ala Met Phe Gly Gly Gly Asn Leu Pro Ala Phe Val Val Gly Ala Val
            485             490             495

Ala Ala Thr Ala Ser Ala Val Leu Ser Phe Thr Leu Leu Pro Ser Pro
        500             505             510

Pro Pro Glu Ala Lys Ile Gly Gly Ser Met Gly Gly His
        515             520             525
```

<210> SEQ ID NO 3
<211> LENGTH: 1773
<212> TYPE: DNA
<213> ORGANISM: Spinacia oleracea

<400> SEQUENCE: 3

```
aaaaatggag aatggtacaa aaagagaagg tttagggaaa cttacagttt catcttctct    60
acaagttgaa cagcctttag caccatcaaa gctatggaaa attatagttg tagcttccat   120
agctgctggt gttcaatttg gttgggctct tcagctctct ttgcttacac cttatgttca   180
attgctcgga attcctcata aatttgcctc ttttatttgg cttttgtggac cgatttctgg   240
tatgattgtt cagccagttg tcggctacta cagtgataat tgctcctccc gtttcggtcg   300
ccgccggcca ttcattgccg ccggagctgc acttgttatg attgcggttt tcctcatcgg   360
attcgccgcc gaccttggtc acgcctccgg tgacactctc ggaaaaggat ttaagccacg   420
tgccattgcc gttttcgtcg tcggcttttg gatccttgat gttgctaaca acatgttaca   480
gggcccatgc agagcactac tggctgatct ctccggcgga aaatccggca ggatgagaac   540
agcaaatgct ttttctcat tcttcatggc cgtcggaaac attctggggt acgccgccgg   600
ttcatattct cacctctta aagtattccc cttctcaaaa accaaagcct gcgacatgta   660
ctgcgcaaat ctgaagagtt gtttcttcat cgctatattc cttttactca gcttaacaac   720
catagcctta accttagtcc gggaaaacga gctcccggag aaagacgagc aagaaatcga   780
cgagaaatta gccggcgccg gaaaatcgaa agtaccgttt tcggtgaaa ttttggggc   840
tttgaaagaa ttacctcgac cgatgtggat tcttctatta gtaacctgtt tgaactggat   900
cgcgtggttt cccttttct tatacgatac agattggatg gctaaggagg ttttcggtgg   960
acaagtcggt gatgcgaggt tgtacgattt gggtgtacgc gctggtgcaa tgggattact  1020
gttgcaatct gtggttctag ggtttatgtc acttgggggtt gaattcttag gaagaagat  1080
tggtggtgct aagaggttat ggggaatttt gaactttgtt ttggctattt gcttggctat  1140
gaccattttg gtcaccaaaa tggccgagaa atctcgccag cacgacccg ccggcacact  1200
tatgggccg acgcctggtg ttaaaatcgg tgccttgctt ctctttgccg cccttggtat  1260
tcctcttgcg gcaaccttta gtattccatt tgctttggca tctatatttt ctagtaatcg  1320
tggttcagga caaggtttgt cactaggagt gctcaatctt gcaattgttg taccacagat  1380
gttggtgtca ctagtaggag ggccatggga tgatttgttt ggaggaggaa acttgcctgg  1440
```

-continued

```
atttgtagtt ggagcagttg cagctgccgc gagcgctgtt ttagcactca caatgttgcc      1500
atctccacct gctgatgcta agccagcagt cgccatgggg ctttccatta ataattaca      1560 aaagaaggag aagaacaact ttttttaat attagtactt ctcttttgta aactttttt       1620 attttagaaa acaaacataa catggaggct atctttacaa gtggcatgtc catgtatctt      1680 cctttttca taaagctctt tagtggaaga agaattagag gaagtttcct tttaatttct      1740
tccaaacaaa tggggtatgt gtagttgttt tca                                  1773
```

<210> SEQ ID NO 4
<211> LENGTH: 516
<212> TYPE: PRT
<213> ORGANISM: Spinacia oleracea

<400> SEQUENCE: 4

```
Met Glu Asn Gly Thr Lys Arg Glu Gly Leu Gly Lys Leu Thr Val Ser
 1               5                  10                  15

Ser Ser Leu Gln Val Glu Gln Pro Leu Ala Pro Ser Lys Leu Trp Lys
            20                  25                  30

Ile Ile Val Val Ala Ser Ile Ala Ala Gly Val Gln Phe Gly Trp Ala
        35                  40                  45

Leu Gln Leu Ser Leu Leu Thr Pro Tyr Val Gln Leu Leu Gly Ile Pro
    50                  55                  60

His Lys Phe Ala Ser Phe Ile Trp Leu Cys Gly Pro Ile Ser Gly Met
65                  70                  75                  80

Ile Val Gln Pro Val Val Gly Tyr Tyr Ser Asp Asn Cys Ser Ser Arg
                85                  90                  95

Phe Gly Arg Arg Arg Pro Phe Ile Ala Ala Gly Ala Ala Leu Val Met
            100                 105                 110

Ile Ala Val Phe Leu Ile Gly Phe Ala Ala Asp Leu Gly His Ala Ser
        115                 120                 125

Gly Asp Thr Leu Gly Lys Gly Phe Lys Pro Arg Ala Ile Ala Val Phe
    130                 135                 140

Val Val Gly Phe Trp Ile Leu Asp Val Ala Asn Asn Met Leu Gln Gly
145                 150                 155                 160

Pro Cys Arg Ala Leu Leu Ala Asp Leu Ser Gly Gly Lys Ser Gly Arg
                165                 170                 175

Met Arg Thr Ala Asn Ala Phe Phe Ser Phe Phe Met Ala Val Gly Asn
            180                 185                 190

Ile Leu Gly Tyr Ala Ala Gly Ser Tyr Ser His Leu Phe Lys Val Phe
        195                 200                 205

Pro Phe Ser Lys Thr Lys Ala Cys Asp Met Tyr Cys Ala Asn Leu Lys
    210                 215                 220

Ser Cys Phe Phe Ile Ala Ile Phe Leu Leu Leu Ser Leu Thr Thr Ile
225                 230                 235                 240

Ala Leu Thr Leu Val Arg Glu Asn Glu Leu Pro Glu Lys Asp Glu Gln
                245                 250                 255

Glu Ile Asp Glu Lys Leu Ala Gly Ala Gly Lys Ser Lys Val Pro Phe
            260                 265                 270

Phe Gly Glu Ile Phe Gly Ala Leu Lys Glu Leu Pro Arg Pro Met Trp
        275                 280                 285

Ile Leu Leu Leu Val Thr Cys Leu Asn Trp Ile Ala Trp Phe Pro Phe
    290                 295                 300

Phe Leu Tyr Asp Thr Asp Trp Met Ala Lys Glu Val Phe Gly Gly Gln
305                 310                 315                 320
```

```
Val Gly Asp Ala Arg Leu Tyr Asp Leu Gly Val Arg Ala Gly Ala Met
                325                 330                 335
Gly Leu Leu Leu Gln Ser Val Val Leu Gly Phe Met Ser Leu Gly Val
            340                 345                 350
Glu Phe Leu Gly Lys Lys Ile Gly Gly Ala Lys Arg Leu Trp Gly Ile
            355                 360                 365
Leu Asn Phe Val Leu Ala Ile Cys Leu Ala Met Thr Ile Leu Val Thr
            370                 375                 380
Lys Met Ala Glu Lys Ser Arg Gln His Asp Pro Ala Gly Thr Leu Met
385                 390                 395                 400
Gly Pro Thr Pro Gly Val Lys Ile Gly Ala Leu Leu Leu Phe Ala Ala
                405                 410                 415
Leu Gly Ile Pro Leu Ala Ala Thr Phe Ser Ile Pro Phe Ala Leu Ala
                420                 425                 430
Ser Ile Phe Ser Ser Asn Arg Gly Ser Gly Gln Gly Leu Ser Leu Gly
            435                 440                 445
Val Leu Asn Leu Ala Ile Val Val Pro Gln Met Leu Val Ser Leu Val
            450                 455                 460
Gly Gly Pro Trp Asp Asp Leu Phe Gly Gly Gly Asn Leu Pro Gly Phe
465                 470                 475                 480
Val Val Gly Ala Val Ala Ala Ala Ser Ala Val Leu Ala Leu Thr
                485                 490                 495
Met Leu Pro Ser Pro Pro Ala Asp Ala Lys Pro Ala Val Ala Met Gly
                500                 505                 510
Leu Ser Ile Lys
            515
```

<210> SEQ ID NO 5
<211> LENGTH: 41
<212> TYPE: DNA
<213> ORGANISM: Spinacia oleracea

<400> SEQUENCE: 5
gagagaggat cctgcaatgg ctgaacgtgt tttgactcgt g                    41

<210> SEQ ID NO 6
<211> LENGTH: 42
<212> TYPE: DNA
<213> ORGANISM: Spinacia oleracea

<400> SEQUENCE: 6
gagagaggat ccttcattca ctcagcagcc aatggaacag ct                   42

<210> SEQ ID NO 7
<211> LENGTH: 45
<212> TYPE: DNA
<213> ORGANISM: Spinacia oleracea

<400> SEQUENCE: 7
gagctgcaga tggcaaacga aactagcgat agacctttgg tcaca                45

<210> SEQ ID NO 8
<211> LENGTH: 42
<212> TYPE: DNA
<213> ORGANISM: Spinacia oleracea

<400> SEQUENCE: 8
gagactagtt tataacctct attttacttc ccttacttgg aa                   42

```
<210> SEQ ID NO 9
<211> LENGTH: 33
<212> TYPE: DNA
<213> ORGANISM: Spinacia oleracea

<400> SEQUENCE: 9
gatccgcggc cgcccggaat tctctagact gca                           33

<210> SEQ ID NO 10
<211> LENGTH: 58
<212> TYPE: DNA
<213> ORGANISM: Spinacia oleracea

<400> SEQUENCE: 10
gaattcatcg atgtcgacca aggaggtcta gatggtacct ctagaagaag ctttcaca  58

<210> SEQ ID NO 11
<211> LENGTH: 14
<212> TYPE: DNA
<213> ORGANISM: Spinacia oleracea

<400> SEQUENCE: 11
aagcttggtc taga                                                14
```

DNA SEQUENCES WITH OLIGOSACCHARIDE TRANSPORTER, PLASMIDS BACTERIA AND PLANTS CONTAINING A TRANSPORTER AS WELL AS A PROCESS FOR THE PREPARATION AND TRANSFORMATION OF YEAST STRAINS FOR IDENTIFICATION OF THE TRANSPORTER

This is a division of application Ser. No. 08/356,340, filed Dec. 21, 1994.

FIELD OF THE INVENTION

The present invention relates to DNA sequences, that contain the coding region of an oligosaccharide transporter, whose introduction in a plant genome modifies the formation and transfer of storage materials in transgenic plants, plasmids, bacteria and plants containing these DNA sequences, a process for the preparation and transformation of yeast strains, that makes possible the identification of the DNA sequences of the plant oligosaccharide transporter of the invention, as well as the use of DNA sequences of the invention.

BACKGROUND OF THE INVENTION

The most important transport metabolite for stored energy in many plants, for example potatoes, is sucrose. In other species, other oligosaccharides can serve this role. In japanese artichokes for example it is stachyose.

The central position of the oligosaccharide transport in the energy content of the plant has already been shown in transgenic plants, in which by expression of an invertase, the sucrose is split into the monosaccharides, leading to considerable changes in its habit (EP 442 592). Because of the significance of sucrose in the formation of storage materials, numerous experiments have been carried out into investigating the biosynthesis or the metabolism of disaccharides. From DE 42 13 444, it is known that the improvement of the storage properties of the harvested parts can be achieved in transgenic potatoes, in which through expression of an apoplastic invertase, the transfer of energy rich compounds to the heterotrophic parts of growing shoots is inhibited.

In spite of much effort, the mechanism for distributing storage materials, such as oligosaccharides in plants has not been clarified and, in order to influence it, it is not yet known, how the sucrose formed in the leaves following photosynthesis, reaches the transport channels of the phloem of the plant and how it is taken up from the storage organs, e.g. the tubers of potato plants or seeds. On isolated plasma membranes of cells of leaf tissue of sugar beet (*Beta vulgaris*) it has been demonstrated that the transport of sucrose through the membrane can be induced by providing an artificial pH gradient and can be intensified by providing an electrochemical potential (Lemoine & Delrot (1989) FEBS letters 249: 129–133). The membrane passage of sucrose follows a Michaelis-Menten kinetic, in which the $k_m$ value of the sucrose transport is around 1 mM (Slone & Buckhout, 1991, Planta 183: 484–589). This form of kinetic indicates the involvement of transporter protein. Experiments on plasma membranes of sugar beet, *Ricinus communis* and *Cyclamen persicum* has shown that the sucrose transport is concerned with a co-transport of protons (Buckhout,1989, Planta 178: 393–399; Williams et al., 1990, Planta 182: 540–545; Grimm et al., 1990, Planta 182: 480–485). The stoichiometry of the co-transport is 1:1 (Bush, 1990, Plant Physiol 93: 1590–1596). Mechanisms have also been proposed however, for transport of the sucrose through the plasmodium of the plant cells (Robards & Lucas, 1990, Ann Rev Plant Physiol 41: 369–419). In spite of the knowledge of the existence of an active transport system, that allows the cells to deliver sucrose to the transport channels, a protein with these kind of properties is not yet known. In N-ethylmaleinimide staining of sugar beet plasma membrane in the presence and absence of sucrose Gallet et al. (1989, Biochem Biophys Acta 978: 56–64) obtained information that a protein of size 42 kDa can interact with sucrose. Antibodies against a fraction of plasma membrane protein of this size range can inhibit the sucrose transport through plasma membranes (Lemoine et al., 1989, Bichem Biophys Acta 978: 65–71). In contrast, information has been obtained (Ripp et al., 1988, Plant Physiol 88: 1435–1445) by the photoaffinity marking of soyabean protein with the sucrose analogue, desoxyazido-hydroxybenzamidosucrose, on the participation of a 62 kDa protein in the transport of sucrose through membranes. An amino acid sequence of a sucrose transporter is not known.

SUMMARY OF THE INVENTION

There are now described DNA sequences which contain the coding region of an oligosaccharide transporter, and whose information contained in the nucleotide sequence allows, by sequence integration in a plant genome, the formation of RNA, by which a new oligosaccharide transport activity can be introduced in the plant cells or an endogenous oligosaccharide transporter activity can be expressed. By the term oligosaccharides transporter is for example to the understood a sucrose transporter from plants such as spinach or potatoes.

DETAILED DESCRIPTION OF THE INVENTION

Figure 1:
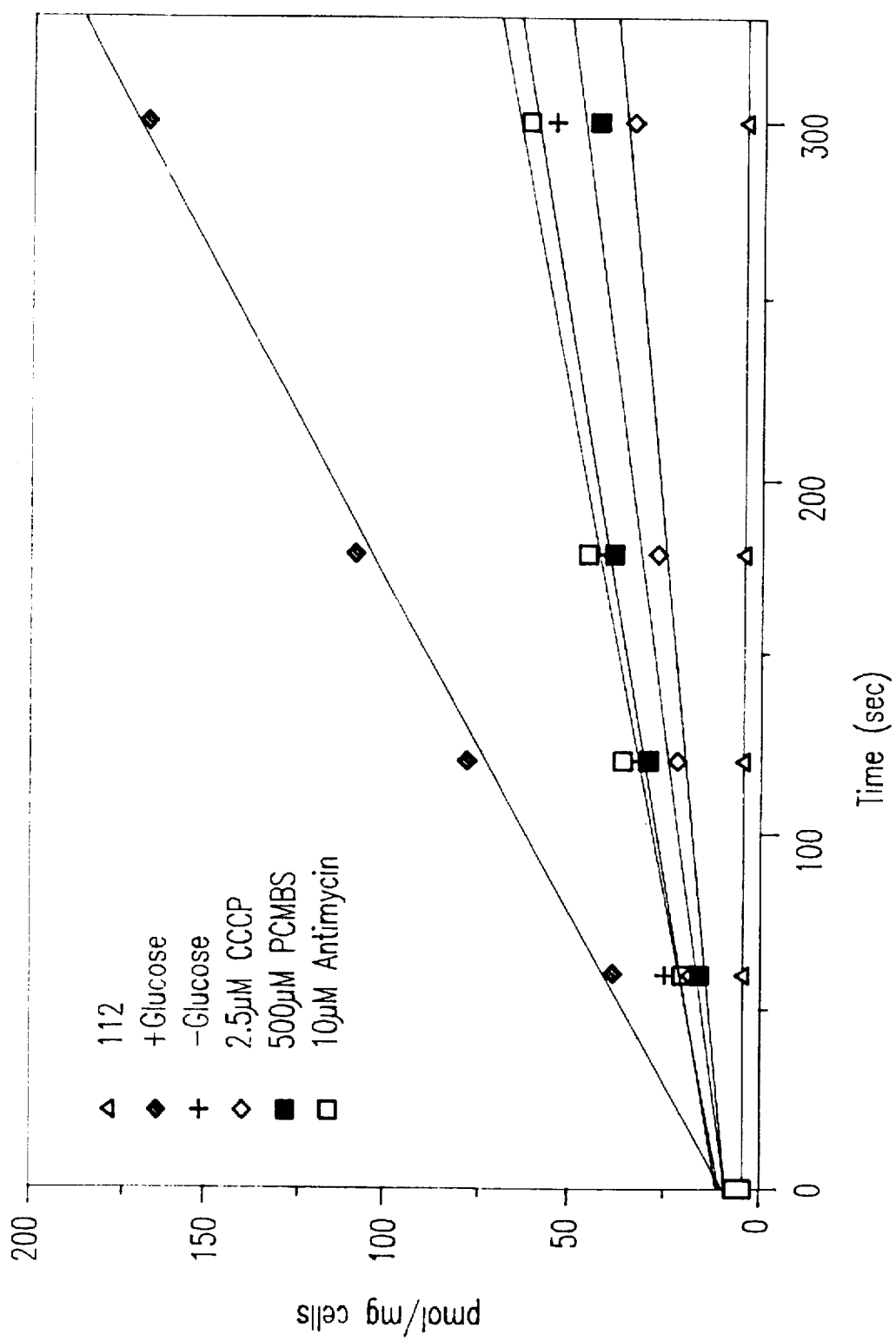
FIG. 1 is a graph of the uptake of sucrose in yeast cells over time.

The identification of the coding region of the oligosaccharide transporter is carried out by a process which allows the isolation of plant DNA sequences which code the transporter molecules by means of expression in specific mutants of yeast *Saccharomyces cerevisiae*. For this, suitable yeast mutants have to be provided which cannot take up a substance for which the coding region of a transporter molecule has to be isolated from a plant gene library. A process is already known for complementation of a potassium transport deficiency in yeast mutants (Anderson et al., 1992, Proc Natl Acad Sci U.S.A. 89: 3736–3740). In this, yeast cDNA sequences for plant mRNA are expressed in yeast mutants by use of expression vectors. Those yeasts which can now take up the substances to be transported into the cells, contain the coding region for a transporter molecule in the expression vector. The known process is however not useful for identification of the coding region for a sucrose transporter, since yeasts contain no endogenous sucrose transporter which could be switched off through mutation. Yeasts code a cleaving invertase, which cleaves extra-cellular sucrose so that hexoses can be taken up from the cells via a hexose transporter.

For the preparation and transformation of yeast strains which serve to identify a plant oligosaccharide transporter:

a) first, a yeast strain with a defective suc2 gene, which cannot be cleaved by invertase, is prepared by homologous recombination and then from this, b) by transformation with a gene for a sucrose synthase activity from plant cells, a yeast strain which can cleave intracellular sucrose is extracted, and c) by transformation of this strain with a plant cDNA library in an expression vector for yeast cells, the DNA sequence, which codes for a plant oligosaccharide transporter, is identified.

The yeast strains obtained from this process, for identification of plant oligosaccharide transporters are for example the yeast strains YSH 2.64-1A-SUSY (DSM 7106) and YSH 2.64-1A-INV (DSM 7105).

With the yeast strain YSH 2.64-1A-SUSY, a DNA sequence for a plant sucrose transporter is identified which has the following sequences.

```
Sucrose-Transporter from spinach (Seq. ID No. 1 No. 2):

AAAAACACAC ACCCAAAAAA AAAACACTAC GACTATTTCA AAAAAAACAT TGTTACTAGA        60

AATCTTATT  ATG GCA GGA AGA AAT ATA AAA AAT GGT GAA AAT AAC             105
           Met Ala Gly Arg Asn Ile Lys Asn Gly Glu Asn Asn
           1               5                   10

AAG ATT GCG GGT TCT TCT CTT CAC TTA GAG AAG AAC CCA ACA ACT            150
Lys Ile Ala Gly Ser Ser Leu His Leu Glu Lys Asn Pro Thr Thr
        15                  20                  25

CCC CCC GAG GCC GAG GCT ACC TTA AAG AAG CTC GGC CTC GTG GCT            195
Pro Pro Glu Ala Glu Ala Thr Leu Lys Lys Leu Gly Leu Val Ala
            30                  35                  40

TCA GTA GCG GCC GGG GTT CAG TTC GGG TGG GCT TTA CAG CTC TCC            240
Ser Val Ala Ala Gly Val Gln Phe Gly Trp Ala Leu Gln Leu Ser
        45                  50                  55

CTA CTG ACC CCG TAC GTC CAA CTA CTG GGC ATT CCC CAC ACT TGG            285
Leu Leu Thr Pro Tyr Val Gln Leu Leu Gly Ile Pro His Thr Trp
        60                  65                  70

GCC GCC TAC ATC TGG TTG TGC GGC CCA ATC TCG GGG ATG ATT GTC            330
Ala Ala Tyr Ile Trp Leu Cys Gly Pro Ile Ser Gly Met Ile Val
        75                  80                  85

CAG CCA TTG GTC GGG TAC TAT AGT GAC CGG TGC ACC TCC CGC TTC            375
Gln Pro Leu Val Gly Tyr Tyr Ser Asp Arg Cys Thr Ser Arg Phe
        90                  95                  100

GGC CGA CGT CGC CCC TTC ATT GCA GCA GGG GCG GCT CTA GTG GCC            420
Gly Arg Arg Arg Pro Phe Ile Ala Ala Gly Ala Ala Leu Val Ala
        105                 110                 115

GTA GCG GTG GGG CTA ATC GGA TTC GCC GCC GAT ATC GGC GCA GCG            465
Val Ala Val Gly Leu Ile Gly Phe Ala Ala Asp Ile Gly Ala Ala
        120                 125                 130

TCG GGT GAT CCA ACG GGA AAC GTG GCA AAA CCC CGG GCC ATC GCG            510
Ser Gly Asp Pro Thr Gly Asn Val Ala Lys Pro Arg Ala Ile Ala
        135                 140                 145

GTG TTT GTG GTC GGG TTT TGG ATC CTC GAC GTG GCT AAC AAC ACC            555
Val Phe Val Val Gly Phe Trp Ile Leu Asp Val Ala Asn Asn Thr
        150                 155                 160

CTG CAA GGC CCA TGC AGG GCG TTG TTA GCA GAC ATG GCC GCC GGG            600
Leu Gln Gly Pro Cys Arg Ala Leu Leu Ala Asp Met Ala Ala Gly
        165                 170                 175

TCG CAA ACC AAA ACC CGG TAC GCT AAC GCC TTC TTC TCC TTC TTC            645
Ser Gln Thr Lys Thr Arg Tyr Ala Asn Ala Phe Phe Ser Phe Phe
        180                 185                 190

ATG GCG TTA GGA AAC ATC GGA GGG TAC GCC GCC GGT TCA TAC AGC            690
Met Ala Leu Gly Asn Ile Gly Gly Tyr Ala Ala Gly Ser Tyr Ser
        195                 200                 205

CGC CTC TAC ACG GTG TTC CCC TTT ACC AAA ACC GCC GCC TGC GAC            735
Arg Leu Tyr Thr Val Phe Pro Phe Thr Lys Thr Ala Ala Cys Asp
        210                 215                 220
```

-continued

```
GTC TAC TGC GCC AAT CTA AAA TCC TGC TTC TTC ATC TCC ATC ACA          780
Val Tyr Cys Ala Asn Leu Lys Ser Cys Phe Phe Ile Ser Ile Thr
        225                 230                 235

CTC CTA ATC GTC CTC ACA ATC CTA GCA CTT TCC GTC GTA AAA GAG          825
Leu Leu Ile Val Leu Thr Ile Leu Ala Leu Ser Val Val Lys Glu
        240                 245                 250

CGT CAA ATC ACA ATC GAC GAA ATC CAA GAA GAA GAA GAC TTA AAA          870
Arg Gln Ile Thr Ile Asp Glu Ile Gln Glu Glu Glu Asp Leu Lys
        255                 260                 265

AAC AGA AAC AAT AGC AGC GGT TGT GCA AGA CTA CCG TTC TTC GGA          915
Asn Arg Asn Asn Ser Ser Gly Cys Ala Arg Leu Pro Phe Phe Gly
        270                 275                 280

CAA TTA ATA GGC GCT CTC AAA GAT CTA CCA AAA CCA ATG CTA ATC          960
Gln Leu Ile Gly Ala Leu Lys Asp Leu Pro Lys Pro Met Leu Ile
        285                 290                 295

CTA TTA CTA GTA ACA GCC CTA AAT TGG ATC GCA TGG TTT CCA TTC         1005
Leu Leu Leu Val Thr Ala Leu Asn Trp Ile Ala Trp Phe Pro Phe
        300                 305                 310

TTG TTG TTC GAT ACT GAT TGG ATG GGT AAA GAA GTG TAC GGT GGT         1050
Leu Leu Phe Asp Thr Asp Trp Met Gly Lys Glu Val Tyr Gly Gly
        315                 320                 325

ACA GTC GGA GAA GGT AAA TTG TAC GAC CAA GGA GTT CAT GCC GGT         1095
Thr Val Gly Glu Gly Lys Leu Tyr Asp Gln Gly Val His Ala Gly
        330                 335                 340

GCC TTA GGT CTG ATG ATT AAC TCC GTT GTC TTA GGT GTT ATG TCG         1140
Ala Leu Gly Leu Met Ile Asn Ser Val Val Leu Gly Val Met Ser
        345                 350                 355

TTG AGT ATT GAA GGT TTG GCT CGT ATG GTA GGC GGT GCT AAA AGG         1185
Leu Ser Ile Glu Gly Leu Ala Arg Met Val Gly Gly Ala Lys Arg
        360                 365                 370

TTA TGG GGA ATT GTC AAT ATT ATT CTT GCT GTT TGT TTA GCT ATG         1230
Leu Trp Gly Ile Val Asn Ile Ile Leu Ala Val Cys Leu Ala Met
        375                 380                 385

ACG GTG TTA GTT ACT AAG TCC GCC GAA CAC TTC CGT GAT AGC CAC         1275
Thr Val Leu Val Thr Lys Ser Ala Glu His Phe Arg Asp Ser His
        390                 395                 400

CAT ATT ATG GGC TCC GCC GTC CCT CCG CCG CCG CCT GCT GGT GTT         1320
His Ile Met Gly Ser Ala Val Pro Pro Pro Pro Pro Ala Gly Val
        405                 410                 415

AAG GGT GGC GCT TTG GCT ATC TTT GCC GTT CTT GGT ATC CCT CTT         1365
Lys Gly Gly Ala Leu Ala Ile Phe Ala Val Leu Gly Ile Pro Leu
        420                 425                 430

GCG ATC ACT TTC AGT ATT CCT TTG GCC TTG GCG TCA ATC TTT TCA         1410
Ala Ile Thr Phe Ser Ile Pro Leu Ala Leu Ala Ser Ile Phe Ser
        435                 440                 445

GCA TCT TCC GGT TCA GGA CAA GGT CTT TCT CTA GGA GTT CTC AAC         1455
Ala Ser Ser Gly Ser Gly Gln Gly Leu Ser Leu Gly Val Leu Asn
        450                 455                 460

CTC GCC ATC GTT GTA CCC CAG ATG TTT GTG TCG GTA ACA AGT GGG         1500
Leu Ala Ile Val Val Pro Gln Met Phe Val Ser Val Thr Ser Gly
        465                 470                 475

CCA TGG GAT GCA ATG TTT GGT GGA GGA AAT TTG CCA GCA TTC GTG         1545
Pro Trp Asp Ala Met Phe Gly Gly Gly Asn Leu Pro Ala Phe Val
        480                 485                 490

GTG GGA GCT GTA GCA GCA ACA GCC AGT GCA GTT CTT TCA TTT ACA         1590
Val Gly Ala Val Ala Ala Thr Ala Ser Ala Val Leu Ser Phe Thr
        495                 500                 505

TTG TTG CCT TCT CCA CCC CCT GAA GCT AAA ATT GGT GGG TCC ATG         1635
Leu Leu Pro Ser Pro Pro Pro Glu Ala Lys Ile Gly Gly Ser Met
        510                 515                 520
```

-continued

```
GGT GGT CAT TAAGAAATTT AATACTACTC CGTACAATTT AAACCCAAAT      1684
Gly Gly His
        525

TAAAAATGAA AATGAAAATT TTTAACCCAT GTTCGTTACG TTGTAATTAG       1734

AGAGAAAAAT GATATATTGA ACGAAGCCGT TAATTTATGC TCCGTTCATC       1784

TTGTAATTCT TTTTCTCTCT GCTTTTTTTT TTTTTTTTTA ACGCGACGTG       1834

TTTTTGAGAT AAGGAAGGGC TAGATCGAGG ATGGGGGAAT TGGCAAGAAA       1884

TTGCTCGGGT ATAAATATTT ATCCCTCTTT GTAATTTTCA GTAACATTTA       1934

ATAGCCAGAA ATCAAAAAGT CAAGAAAAAT CGAAA                       1969
```

Sucrose Transporter from potato (Seq-ID No. 3 and No. 4):

```
                                                      AAAA         4

ATG GAG AAT GGT ACA AAA AGA GAA GGT TTA GGG AAA CTT ACA GTT        49
Met Glu Asn Gly Thr Lys Arg Glu Gly Leu Gly Lys Leu Thr Val
                  5                  10                 15

TCA TCT TCT CTA CAA GTT GAA CAG CCT TTA GCA CCA TCA AAG CTA        94
Ser Ser Ser Leu Gln Val Glu Gln Pro Leu Ala Pro Ser Lys Leu
                 20                  25                 30

TGG AAA ATT ATA GTT GTA GCT TCC ATA GCT GCT GGT GTT CAA TTT       139
Trp Lys Ile Ile Val Val Ala Ser Ile Ala Ala Gly Val Gln Phe
                 35                  40                 45

GGT TGG GCT CTT CAG CTC TCT TTG CTT ACA CCT TAT GTT CAA TTG       184
Gly Trp Ala Leu Gln Leu Ser Leu Leu Thr Pro Tyr Val Gln Leu
                 50                  55                 60

CTC GGA ATT CCT CAT AAA TTT GCC TCT TTT ATT TGG CTT TGT GGA       229
Leu Gly Ile Pro His Lys Phe Ala Ser Phe Ile Trp Leu Cys Gly
                 65                  70                 75

CCG ATT TCT GGT ATG ATT GTT CAG CCA GTT GTC GGC TAC TAC AGT       274
Pro Ile Ser Gly Met Ile Val Gln Pro Val Val Gly Tyr Tyr Ser
                 80                  85                 90

GAT AAT TGC TCC TCC CGT TTC GGT CGC CGC CGG CCA TTC ATT GCC       319
Asp Asn Cys Ser Ser Arg Phe Gly Arg Arg Arg Pro Phe Ile Ala
                 95                 100                105

GCC GGA GCT GCA CTT GTT ATG ATT GCG GTT TTC CTC ATC GGA TTC       364
Ala Gly Ala Ala Leu Val Met Ile Ala Val Phe Leu Ile Gly Phe
                110                 115                120

GCC GCC GAC CTT GGT CAC GCC TCC GGT GAC ACT CTC GGA AAA GGA       409
Ala Ala Asp Leu Gly His Ala Ser Gly Asp Thr Leu Gly Lys Gly
                125                 130                135

TTT AAG CCA CGT GCC ATT GCC GTT TTC GTC GTC GGC TTT TGG ATC       454
Phe Lys Pro Arg Ala Ile Ala Val Phe Val Val Gly Phe Trp Ile
                140                 145                150

CTT GAT GTT GCT AAC AAC ATG TTA CAG GGC CCA TGC AGA GCA CTA       499
Leu Asp Val Ala Asn Asn Met Leu Gln Gly Pro Cys Arg Ala Leu
                155                 160                165

CTG GCT GAT CTC TCC GGC GGA AAA TCC GGC AGG ATG AGA ACA GCA       544
Leu Ala Asp Leu Ser Gly Gly Lys Ser Gly Arg Met Arg Thr Ala
                170                 175                180

AAT GCT TTT TTC TCA TTC TTC ATG GCC GTC GGA AAC ATT CTG GGG       589
Asn Ala Phe Phe Ser Phe Phe Met Ala Val Gly Asn Ile Leu Gly
                185                 190                195

TAC GCC GCC GGT TCA TAT TCT CAC CTC TTT AAA GTA TTC CCC TTC       634
Tyr Ala Ala Gly Ser Tyr Ser His Leu Phe Lys Val Phe Pro Phe
                200                 205                210

TCA AAA ACC AAA GCC TGC GAC ATG TAC TGC GCA AAT CTG AAG AGT       679
Ser Lys Thr Lys Ala Cys Asp Met Tyr Cys Ala Asn Leu Lys Ser
                215                 220                225
```

-continued

| | |
|---|---|
| TGT TTC TTC ATC GCT ATA TTC CTT TTA CTC AGC TTA ACA ACC ATA<br>Cys Phe Phe Ile Ala Ile Phe Leu Leu Leu Ser Leu Thr Thr Ile<br>230                        235                    240 | 724 |
| GCC TTA ACC TTA GTC CGG GAA AAC GAG CTC CCG GAG AAA GAC GAG<br>Ala Leu Thr Leu Val Arg Glu Asn Glu Leu Pro Glu Lys Asp Glu<br>245                       250                  255 | 769 |
| CAA GAA ATC GAC GAG AAA TTA GCC GGC GCC GGA AAA TCG AAA GTA<br>Gln Glu Ile Asp Glu Lys Leu Ala Gly Ala Gly Lys Ser Lys Val<br>260                     265                270 | 814 |
| CCG TTT TTC GGT GAA ATT TTT GGG GCT TTG AAA GAA TTA CCT CGA<br>Pro Phe Phe Gly Glu Ile Phe Gly Ala Leu Lys Glu Leu Pro Arg<br>275                   280                285 | 859 |
| CCG ATG TGG ATT CTT CTA TTA GTA ACC TGT TTG AAC TGG ATC GCG<br>Pro Met Trp Ile Leu Leu Leu Val Thr Cys Leu Asn Trp Ile Ala<br>290                   300               305 | 904 |
| TGG TTT CCC TTT TTC TTA TAC GAT ACA GAT TGG ATG GCT AAG GAG<br>Trp Phe Pro Phe Phe Leu Tyr Asp Thr Asp Trp Met Ala Lys Glu<br>310                   315               320 | 949 |
| GTT TTC GGT GGA CAA GTC GGT GAT GCG AGG TTG TAC GAT TTG GGT<br>Val Phe Gly Gly Gln Val Gly Asp Ala Arg Leu Tyr Asp Leu Gly<br>325                   330               335 | 994 |
| GTA CGC GCT GGT GCA ATG GGA TTA CTG TTG CAA TCT GTG GTT CTA<br>Val Arg Ala Gly Ala Met Gly Leu Leu Leu Gln Ser Val Val Leu<br>340                   345               350 | 1039 |
| GGG TTT ATG TCA CTT GGG GTT GAA TTC TTA GGG AAG AAG ATT GGT<br>Gly Phe Met Ser Leu Gly Val Glu Phe Leu Gly Lys Lys Ile Gly<br>355                   360               370 | 1084 |
| GGT GCT AAG AGG TTA TGG GGA ATT TTG AAC TTT GTT TTG GCT ATT<br>Gly Ala Lys Arg Leu Trp Gly Ile Leu Asn Phe Val Leu Ala Ile<br>375                   380               385 | 1129 |
| TGC TTG GCT ATG ACC ATT TTG GTC ACC AAA ATG GCC GAG AAA TCT<br>Cys Leu Ala Met Thr Ile Leu Val Thr Lys Met Ala Glu Lys Ser<br>390                   395               400 | 1174 |
| CGC CAG CAC GAC CCC GCC GGC ACA CTT ATG GGG CCG ACG CCT GGT<br>Arg Gln His Asp Pro Ala Gly Thr Leu Met Gly Pro Thr Pro Gly<br>405                   410               415 | 1219 |
| GTT AAA ATC GGT GCC TTG CTT CTC TTT GCC GCC CTT GGT ATT CTT<br>Val Lys Ile Gly Ala Leu Leu Leu Phe Ala Ala Leu Gly Ile Pro<br>420                   425               430 | 1264 |
| CTT GCG GCA ACT TTT AGT ATT CCA TTT GCT TTG GCA TCT ATA TTT<br>Leu Ala Ala Thr Phe Ser Ile Pro Phe Ala Leu Ala Ser Ile Phe<br>435                   440               445 | 1309 |
| TCT AGT AAT CGT GGT TCA GGA CAA GGT TTG TCA CTA GGA GTG CTC<br>Ser Ser Asn Arg Gly Ser Gly Gln Gly Leu Ser Leu Gly Val Leu<br>450                     455               460 | 1354 |
| AAT CTT GCA ATT GTT GTA CCA CAG ATG TTG GTG TCA CTA GTA GGA<br>Asn Leu Ala Ile Val Val Pro Gln Met Leu Val Ser Leu Val Gly<br>465                   470               475 | 1399 |
| GGG CCA TGG GAT GAT TTG TTT GGA GGA GGA AAC TTG CCT GGA TTT<br>Gly Pro Trp Asp Asp Leu Phe Gly Gly Gly Asn Leu Pro Gly Phe<br>480                   485               490 | 1444 |
| GTA GTT GGA GCA GTT GCA GCT GCC GCG AGC GCT GTT TTA GCA CTC<br>Val Val Gly Ala Val Ala Ala Ala Ser Ala Val Leu Ala Leu<br>495                   500               505 | 1489 |
| ACA ATG TTG CCA TCT CCA CCT GCT GAT GCT AAG CCA GCA GTC GCC<br>Thr Met Leu Pro Ser Pro Pro Ala Asp Ala Lys Pro Ala Val Ala<br>510                   515               520 | 1534 |
| ATG GGG CTT TCC ATT AAA TAATTACAAA AGAAGGAGAA GAACAACTTT<br>Met Gly Leu Ser Ile Lys<br>525 | 1582 |

```
-continued
TTTTTAATAT TAGTACTTCT CTTTTGTAAA CTTTTTTTAT TTTAGAAAAC            1632

AAACATAACA TGGAGGCTAT CTTTACAAGT GGCATGTCCA TGTATCTTCC            1682

TTTTTTCATA AAGCTCTTTA GTGGAAGAAG AATTAGAGGA AGTTTCCTTT            1732

TAATTTCTTC CAAACAAATG GGGTATGTGT AGTTGTTTTC A                     1773
```

The identified DNA sequences can be introduced into plasmids and thereby be combined with steering elements for expression in eukaryotic cells (see Example 5). These steering elements are on the one hand transcription promoters, and on the other hand transcription terminators. With the DNA sequences of the invention contained on the plasmids, eukaryotic cells can be transformed, with the aim of expression of a translatable mRNA which makes possible the synthesis of a sucrose transporter in the cells or with the aim of expression of a non-translatable RNA, which prevents synthesis of an endogenous sucrose transporter in the cells. By expression of an RNA corresponding to the inventive sequences of the oligosaccharide transporter, a modification of the plant carbohydrate metabolism is possible, which can be of significance in that an improvement in the delivery of storage substances in the harvested parts results in an increase in yield of agricultural plants. The possibility of forcing the up-take of storage materials in individual organs allows the modification of the whole plant by which the growth of individual tissues, for example leaves, is slowed down, whilst the growth of the harvested parts is increased. For this, one can imagine a lengthening of the vegetative phase of crops, which leads to an increased formation of storage substances.

Processes for the genetic modification of dicotyledonous and monocotyledonous plants are already known, (see for example Gasser, C. S., Fraley, R. T., 1989, Science 244: 1293–1299; Potrykus, 1991, Ann Rev Plant Mol Biol Plant Physiol 42: 205–225). For expression in plants—the coding sequences must be coupled with the transcriptional regulatory elements. Such elements called promoters, are known (EP 375091).

Further, the coding regions must be provided with transcription termination signals with which they can be correctly transcribed. Such elements are also described (see Gielen et al., 1989. EMBO J 8: 23–29). The transcriptional start region can be native and/or homologous as well as foreign and/or heterologous to the host plant. If desired, termination regions are interchangeable with one another. The DNA sequence of the transcription starting and termination regions can be prepared synthetically or obtained naturally, or obtained from a mixture of synthetic and natural DNA constituents. For introduction of foreign genes in higher plants, a large number of cloning vectors are available that include a replication signal for E. coli and a marker which allows a selection of the transformed cells. Examples of such vectors are pBR 322, pUC-Series, M13 mp-Series, pACYC 184 etc. Depending on the method of introduction of the desired gene in the plants, other DNA sequences may be suitable. Should the Ti- or Ri-plasmid be used, e.g. for the transformation of the plant cell, then at least the right boundary, often however both the right and left boundary of the Ti- and Ri-Plasmid T-DNA, is attached, as a flanking region, to the gene being introduced. The use of T-DNA for the transformation of plants cells has been intensively researched and is well described in EP 120 516; Hoekama, In: The Binary Plant Vector System. Offset-drukkerij Kanters B. V. Alblasserdam, (1985), Chapter V; Fraley, et al., Crit. Rev. Plant Sci., 4:1–46 and An et al. (1985) EMBO J. 4: 277–287. Once the introduced DNA is integrated in the genome, it is generally stably incorporated and remains also in the offspring of the original transformed cells. It normally contains a selection marker, which induces resistance in the transformed plant cells against a biocide or antibiotic such as kanamycin, G 418, bleomycin, hygromycin or phosphinotricin etc. The individual marker employed should therefore allow the selection of transformed cells from cells which lack the introduced DNA.

For the introduction of DNA into a plant host cell, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium, which contains antibiotics or biocides for the selection. The resulting plants can then be tested for the presence of introduced DNA. No special demands are placed on the plasmids in injection and electroporation. Simple plasmids, such as e.g. pUC-derivatives can be used. Should however whole plants be regenerated from such transformed cells the presence of a selectable marker gene is necessary. The transformed cells grow within the plants in the usual manner (see also McCormick et al.(1986) Plant Cell Reports 5: 81–84). These plants can be grown normally and crossed with plants, that possess the same transformed genes or different genes. The resulting hybrid individuals have the corresponding phenotypical properties.

The DNA sequences of the invention can also be introduced in plasmids and thereby combined with steering elements for an expression in prokaryotic cells. The formation of a translatable RNA sequence of a eukaryotic sucrose transporter from bacteria leads, in spite of the considerable differences in the membrane structures of prokaryotes and eukaryotes, to prokaryotes which are able to take up sucrose. This makes possible the production of technically interesting bacterial strains, which could be grown on the relatively cheap substrate sucrose (see Example 5). For example, the production of polyhydroxybutyric acid in the bacteria *Alkaligenes eutrophus* is described (Steinbuchel & Schubert, 1989, Arch Microbiol 153: 101–104). The bacterium only uses however a very limited selection of substrates. The expression of a gene for a sucrose transporter, amongst others, in *Alkaligenes eutrophus* would therefore be of great interest.

The DNA sequences of the invention can also be introduced in plasmids which allow mutagenesis or a sequence modification through recombination of DNA sequences in prokaryotic or eukaryotic systems. In this way the specificity of the sucrose transporter can be modified.

By using standard processes (see Sambrook et al., 1989, Molecular Cloning: A Laboratory Manual, 2. Edn., Cold Spring Harbor Laboratory Press, New York, U.S.A.), base exchanges can be carried out or natural or synthetic sequences can be added. For binding DNA fragments with one another, adaptors or linkers can be introduced on the fragments. Further, manipulations can be carried which prepare suitable restriction cleavage sides or remove the excess DNA or restriction cleavage sites. Where insertions, deletions or substitutions such as, for example transitions and transversions, are to be carried out, in vitro mutagenesis, primer repair, restrictions or ligations can be used. For methods of analysis, in general a sequence analysis, restriction analysis and other biochemical molecular biological methods can be used. After each manipulation, the DNA sequence, used, can be cleaved and bound with another DNA sequence. Each plasmid sequence can be cloned in the same or different plasmids.

Derivatives or parts of the DNA sequences and plasmids of the invention can also be used for the transformation of prokaryotic and eukaryotic cells. Further, the DNA sequences of the invention can be used according to standard processes for the isolation of similar sequences on the genome of plants of various species, which also code for sucrose or other oligosaccharide transporter molecules. With these sequences, constructs for the transformation of plant cells can be prepared which modify the transport process in transgenic plants.

In order to specify related DNA sequences, gene libraries must first be prepared, which are representative of the content in genes of a plant type or of the expression of genes in a plant type. The former are genomic libraries, while the latter are cDNA libraries. From these, related sequences can be isolated using the DNA sequences of the invention as probes. Once the related gene has been identified and isolated, a determination of the sequence and an analysis of the properties of the proteins coded from this sequence is possible.

In order to understand the examples forming the basis of this invention all the processes necessary for these tests and which are known per se will first be listed:

1. Cloning Process

For cloning, there was used the phage Lambda ZAP II, as well as the vector pBluescriptSK (Short et al., 1988, Nucl Acids Res 16: 7583–7600).

For the transformation of yeasts, the vectors YIplac 128 and YEplac 112 (Gietz & Sugino, 1988, Gene 74: 527–534) were used.

For the plant transformation, the gene constructs in the binary vector pBinAR (Höfgen & Willmitzer, 1990, Plant Sci 66: 221–230) were cloned.

2. Bacterial and Yeast Strains

For the pBbluescriptSK vector as well as for PBinAR constructs, the *E. coli* strain XL1blue (Bullock et al., 1987, Biotechniques, 5, 376–378) was used.

As starting strain for the production of yeast strain YSH 2.64-1A-susy of the invention, the strain YSH 2.64-1A (Gozalbo & Hohmann, 1990, Curr Genet 17: 77–79) was used.

The transformation of the plasmid in potato plant was carried out using *Agrobacterium tumefaciens* strain LBA4404 (Bevan (1984) Nucl. Acids Res 12: 8711–8720).

3. Transformation of *Agrobacterium tumefaciens*

The transfer of the DNA in the Agrobacteria was carried out by direct transformation by the method of Höfgen & Willmitzer (1988, Nucleic Acids Res 16: 9877). The plasmid DNA of the transformed Agrobacterium was isolated in accordance with the method of Birnboim and Doly (1979) (Nucl Acids Res 7: 1513–1523) and was analysed by gel electrophoresis after suitable restriction cleavage.

4. Plant Transformation

Ten small leaves, wounded with a scalpel, of a sterile potato culture were placed in 10 ml of MS medium with 2% sucrose containing 30–50 µl of an *Agrobacterium tumefaciens* overnight culture grown under selection. After 3–5 minutes gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.

Deposits

The following plasmids and yeast strains were deposited at the Deutschen Sammlung von Mikroorganismen (DSM) in Braunschweig, Germany on the 12.06.1992 (deposit number):

| Plasmid | pSK-S21 | (DSM 7115) |
| Yeast strain | YSH 2.64-1A-SUSY | (DSM 7106) |
| Yeast strain | YSH 2.64-1A-INV | (DSM 7105) |

Description of the Figures

FIG. 1

Time pattern of the uptake of sucrose in yeast cells. "pmol/mg cells"=amount of the $^{14}$C-labelled sucrose in pmol taken up in relation to the moisture weight of the yeast cells per mg; "112"=starting strain (without transporter); "+Glucose"=pre-incubation of the cells in a medium of 10 mM glucose; "–Glucose"=no pre-incubation of the cells; "2.5 µMCCCP"=coincubation with the inhibitor, carbonyl cyanide m-chlorophenylhydrazone (CCCP) in a concentration of 2.5 µM; "500 µMPCMBS"=coincubation with the inhibitor p-chloromercuribenzenesulfonic acid (PCMBS) in a concentration of 500 µM; "10 µM Antimycin"= coincubation with the inhibitor antimycin in a concentration of 10 µM.

FIG. 2

Cloning of the plasmid pMA5-INV. Shows the insertion of 2.4 kb size HindIII Fragment from pSEYC 306-1 in pMA5-10 (SEQ.ID.NOS.: 10 and 11).

FIG. 3

Shows the plasmid pBinAR-S21.

In this:

| CaMV 35S promoter: | promoter of the gene for the 35S RNA of the cauliflower mosaic virus |
|---|---|
| A: | coding region of the sucrose transporter in spinach, orientation in the reading direction |
| OCS: | terminator of the octopine synthase gene from *Agrobacterium tumefaciens* |
| SmaI, NotI, BamHI: | Cleavage positions of restriction enzymes |

FIG. 4:

Shows the plasmid pBinAR-P62-anti.

In this:

| CaMV 35S promoter: | promoter of the gene for the 35S RNA of the cauliflower mosaic virus |
|---|---|
| OCS: | terminator of the octopine synthase gene from *Agrobacterium tumefaciens* |
| SMaI, SacI, BamHI, XbaI: | Cleavage positions of restriction enzymes |

FIG. 5:

Content of various carbohydrates in leaves of BinAR-P62-anti transformands.

In this

| fru: | fructose |
|---|---|
| suc: | sucrose |
| sta: | starch |
| control: | untransformed starting plants |
| sp-5 to sp-43: | transformands with individual numbers |

FIG. 6:

Efflux of carbohydrates from petioles of BinAR-P62-anti transformands

| wt: Wild type | |
|---|---|
| sp-5 to sp-43: | transformands with individual numbers |

The following examples describe the preparation of the yeast strains, the identification as well as the function and use of a plant sucrose transporter.

EXAMPLE 1

Preparation of the yeast strains YSH 2.64-1A-SUSY and YSH 2.64-1A-INV

The yeast strain YSH 2.64-1A has the features suc2-, ma10, leu2, trp1 (Gozalbo & Hohmann, 1990, Curr Genet 17: 77–79). In order to introduce a sucrose cleaving enzymatic activity in this strain, it was transformed with the integrative plasmid YIplac128A2-SUSY, that contains the coding region of the sucrose synthase from potato as a fusion to the promoter of the gene for alcohol dehydrogenase from yeast. The plasmid YIplac 128A2-SUSY was prepared as follows. The plasmid YIplac128 (Gietz & Sugino, 1988, Gene 74: 527–534) was shortened by cleavage with PstI and EcoRI, degradation and/or filling in of overhanging single strands and ligation in the region of the polylinker. In the remaining SphI cleavage position, a 728 bp cassette was inserted with the promoter of alcohol dehydrogenase from the plasmid pVT102U (Vernet et al., 1987, Gene 52: 225–233). In this way YIplac128A2 was obtained. The coding region of the sucrose synthase was amplified by polymerase chain reaction with the oligonucleotides SUSY1 (SEQ.ID.NO.: 5) (GAGAGAGGATCCTGCAA-TGGCTGAACGTGTTTTGACTCGTG) and SUSY2 (SEQ.ID.NO.: 6) (GAGAGAGGATCCTTCAT-TCACTCAGCAGCCAATGGAACAGCT) to a lambda clone of sucrose synthase from potato (Salanoubat & Belliard, 1987, Gene 60: 47–56). From the product, the coding region was prepared as BamHI fragment and inserted in the BamHI cleavage site of the polylinker of the cassette. The yeast strain YSH 2.64-1A was transformed with the so prepared plasmid YIplac128A2-SUSY. Since the plasmid does not carry the 2 μ region, it cannot be autonomically replicated in yeast. Therefore such transformands only acquire leucine auxotrophy, which at least partially chromosomally integrate the plasmid-DNA.

Leucine autotroph colonies were analysed for expression of the sucrose synthase gene. For this, cells of a 5 ml liquid culture were decomposed by addition of glass pearls with vigorous shaking, and then, after centrifuging, total protein from the supernatant was added for an enzyme activity measurement. The activity of the expressed sucrose synthase contains 25 mU/mg protein.

In a similar manner an invertase activity was introduced in the yeast strain YSH 2.64-1A, in which by help of the plasmid YIplac128A1-INV, a gene for a cytosolic, noncleavable invertase was chromosomally integrated in the yeast genome. YIplac128A1-INV contains instead of the coding region for sucrose synthase, an invertase gene, which lacks the signal sequence for export of the gene product. The precursor of the plasmid is the plasmid YIplac128A1, which differs from YIplac128A2 in the orientation of the polylinker in the cassette with the promoter of the alcohol dehydrogenase gene. The cassette for this plasmid derives from the plasmid pVT100U (Vernet et al., 1987, Gene 52: 225–233). The coding region of the invertase was obtained on the DNA of the suc2 gene by polymerase chain reaction with the oligonucleotides INV3 (SEQ.ID.NO.: 7) (GAGCTGCAGATGGCAAAC-GAAACTAGCGATAGACCTTTGGTCACA) and INV4 (SEQ.ID.NO.: 8) (GAGACTAGTTTATAACCTC-TATTTTACTTCCCTTACTTGGAA). The coding region was ligated as PstI/SpeI fragment in the linearised vector YIplac128A1den using PstI and XbaI. A test of the enzymatic activity of the invertase activity expressed in the yeast cells, resulted in an enzyme activity of 68 mU/mg total protein from yeast cells.

EXAMPLE 2

Cloning of the cDNA Plant Sucrose Transporter

From polyadenylated RNA from leaf tissue of growing spinach and potato plants, a library of the cDNA in the phage Lambda ZAP II library was prepared. From 500,000 Pfu, the phage DNA was prepared and purified using a caesium chloride sarcosyl gradient. After cleaving the phage DNA with the enzyme NotI, insertions from the size regions above and below 1.5 kbp were prepared on a 1% agarose gel and ligated in the NotI cleavage sites of the expressions vector YEplac112A1NE. The vector is a derivative of the vector YEplac 112 (Gozalbo & Hohmann, 1990, Curr Genet 17: 77–79), with which, as described in Example 1, the polylinker was exchanged with a cassette with the promoter of the alcohol dehydrogenase gene. The polylinker of the cassette was again removed by cleavage with the enzymes PstI and XbaI and replaced by a double stranded oligonucleotide that introduces a NotI and EcoRI cleavage site (SEQ.ID.NO.: 9: GATCCGCGGCCGCCCGGAATTCTCTAGACTGCA).

Approximately 90,000 clones for the size region below 1.5 kbp and approximately 40,000 clones for the size region above 1.5 kbp were obtained by transformation in E. coli. From these, plasmid DNA was prepared. 2 μg DNA was transformed fourteen times in the yeast strain YSH2.64-1A suc-.susy. Transformands were grown on a medium containing 2% glucose, and five to ten thousand of each were washed off with agar plate liquid medium and plated out on sucrose containing medium. Those colonies, which could be grown faster were further analysed. The insertion in the vector YEplac112A1NE of transformands S21 or P62 (YEplac112A1NE-S21) were sequenced. The sequences are given above.

EXAMPLE 3

Analysis of Sucrose Metabolising Yeast Transformands

The yeast transformand YEplac112A1NE-S21, corresponding to that obtained in Example 2, was grown in liquid medium until the culture had reached the logarithmic phase.

After centrifuging the culture, the cells were subjected to a pre-incubation for 5 minutes in a glucose containing medium and then taken up in a medium containing $^{14}C$-labelled sucrose. The uptake of the labelled sucrose was measured by the process described by Cirillo (1989, Meth Enzymol 174: 617–622). The uptake of the labelled sucrose without preincubation with glucose was compared with that with co-incubation with the inhibitors carbonyl cyanide m-chlorophenylhydrazone (CCCP), p-chloromercuribenzenesulfonic acid (PCMBS) and antimycin. The time pattern is shown in FIG. 1. The calculated reduction of the sucrose uptake by the inhibitors is shown in table I. A competition experiment with various sugars as competitor for the labelled sucrose, from which the specificity of the transporter can be read off, is shown in table II.

Analogous measurements were carried out with the yeast strain YEplac112A1NE-P62. These gave similar results.

EXAMPLE 4

Figure 2:
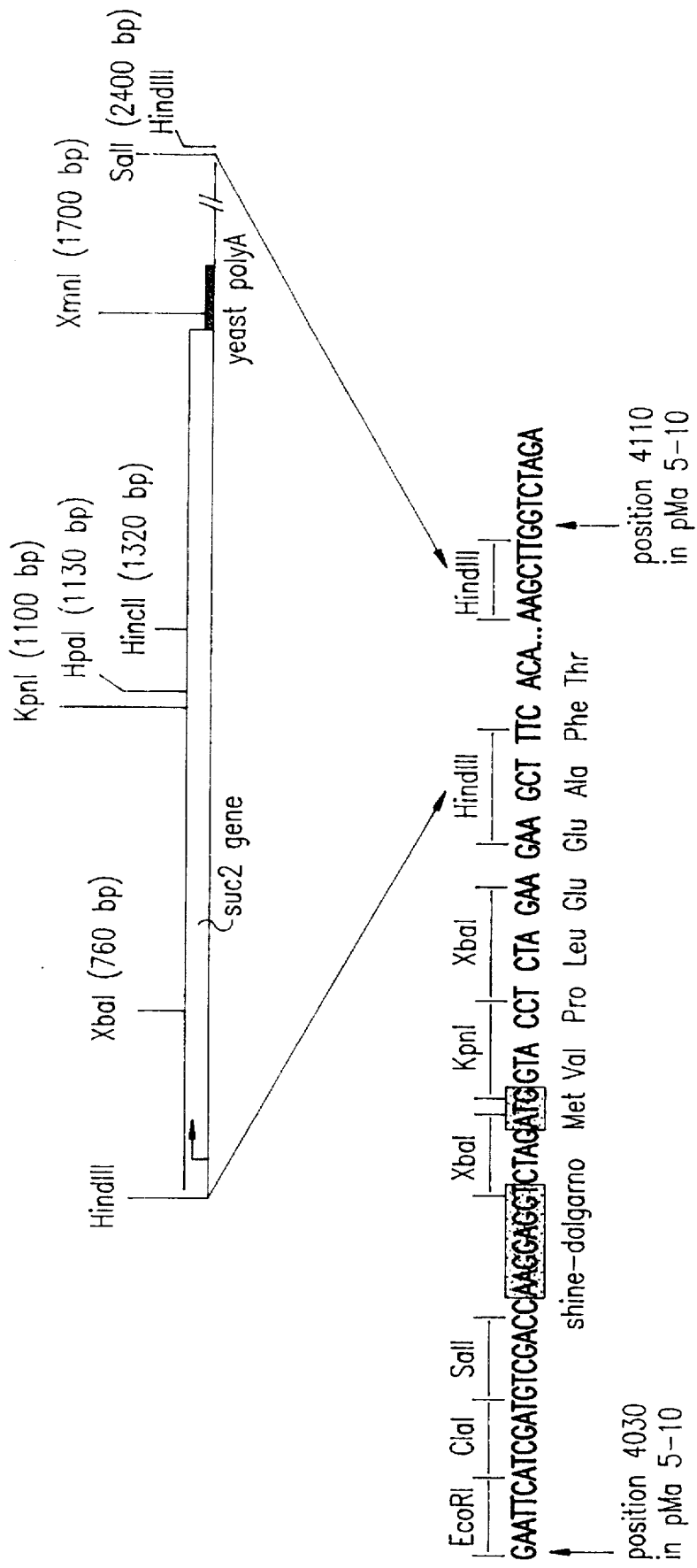
FIG. 2 shows the cloning of the plasmid pMA5-INV.

Transformation of bacterial strains with DNA sequences for expression of a sucrose transporter activity In order to be able to metabolise taken-up sucrose, bacterial cells are needed which have an enzymatic activity for cleavage of the monosaccharide. To introduce such an activity, bacteria were transformed by the plasmid pMA5-INV and tested for invertase activity. The plasmid pMA5-INV was prepared as follows. The plasmid pMA5-10 (Stanssens et al., 1989, Nucl Acids Res 17: 4441–4454) was linearised at the HindIII cleavage site of the polylinker. The 2.4 kb HindIII fragment of the plasmid pSEYC306-1 (Taussig & Carlson, 1983, Nucl Acids Res 11: 1943–1954) was cloned in the HindIII cleavage site. The corresponding cutout of the plasmid is shown in FIG. 2. The enzymatic activity of the invertase in bacteria cells, transformed with the plasmid pMA5-INV was determined in a gel electrophoresis activity test, in known manner. The possibility of the formation of a functional sucrose transporter though expression of a plant cDNA in bacteria cells was tested by transformation of E. coli with the plasmid pSK-S21. The plasmid is described Example 3. After transformation of bacteria cells with pSK-S21, tests for sucrose uptake were carried out.

EXAMPLE 5

Figure 3:
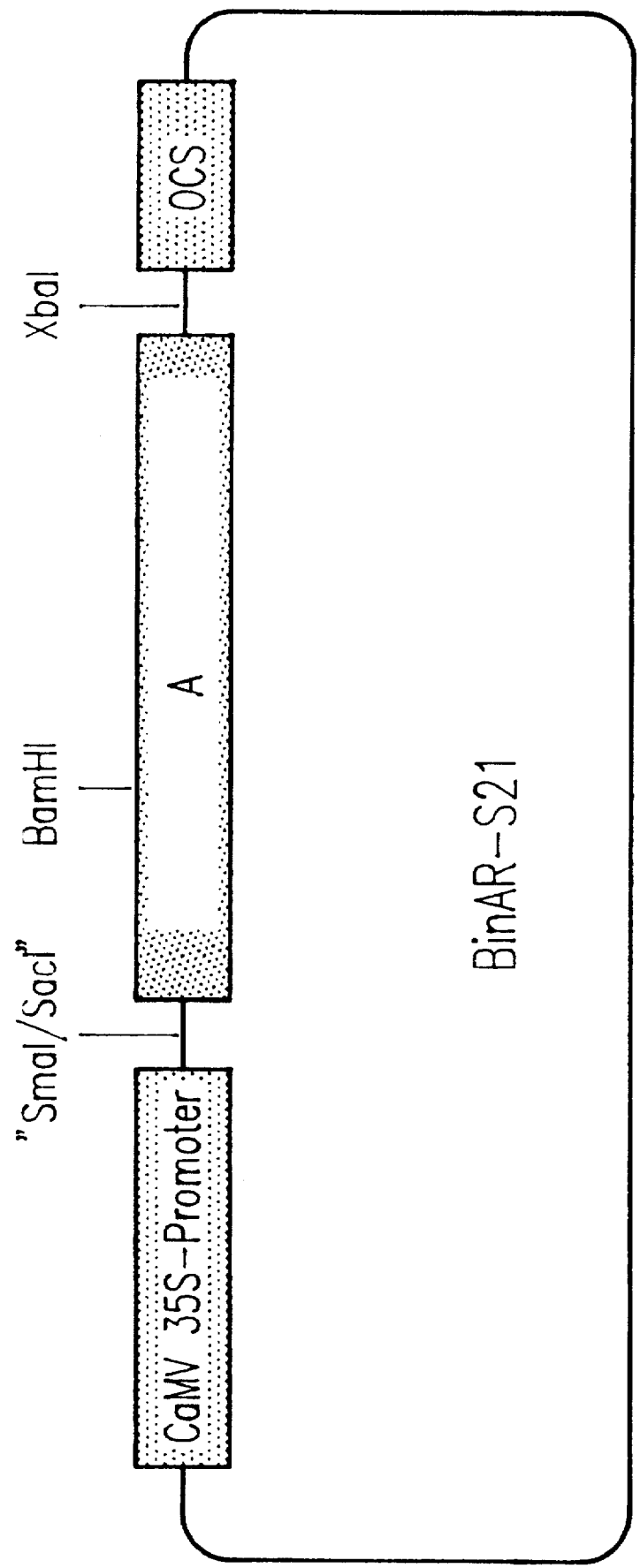
FIG. 3 is a diagram of the plasmid pBinAR-S21.
Figure 4:
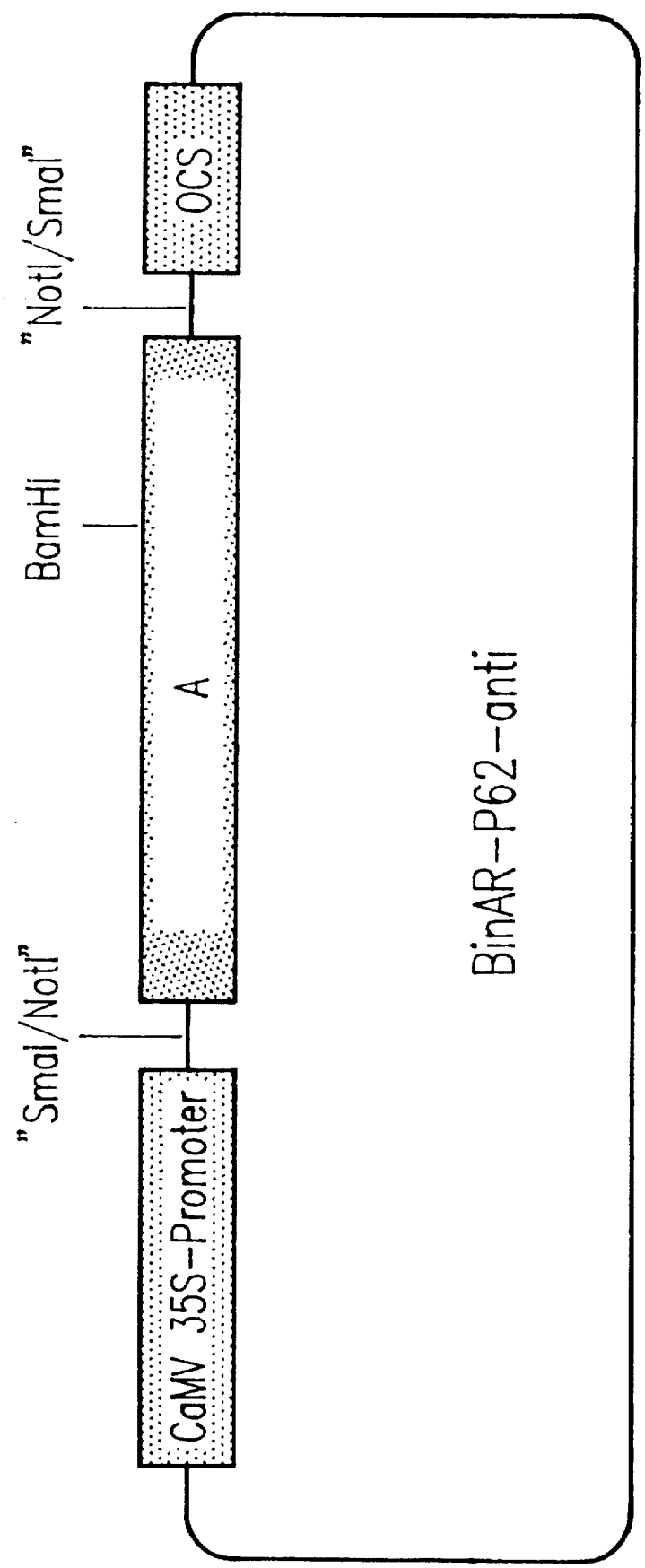
FIG. 4 is a diagram of the plasmid pBinAR-P62-anti.

Transformation of Plants with a Construct for Over-Expression of the Coding Region of the Sucrose Transporter From the vectors YEplac 112A1NE-S21 and YEplac 112A1NE-P62, which contain, as inserts, the cDNA for the sucrose transporter from spinach and/or potato (see Examples 2 and 3), the inserts after NotI cleavage were isolated and ligated in the NotI cleavage site of the plasmids pBluescript-SK (pSK-S21 and/or pSK-P62). For pSK-S21, the insert was prepared as a SacI/XbaI fragment and cloned, after filling in the overhanging single strand-DNA, in the "sense" orientation in pBinAR (Höfgen & Willmitzer, 1990, Plant Sci 66: 221–230) which was previously cleaved with the enzymes SmaI and XbaI. The resulting plasmid pBinAR-S21 (see FIG. 3) can be inserted for transformation of plants in order to over-express the sucrose transporter. For pSK-P62, the insert was isolated as a 1.7 kbp NotI fragment and cloned in an "antisense" orientation in the SmaI cleavage site of the binary vector pBinAR, resulting in pBinAR-P62-anti (see FIG. 4). This plasmid is suitable for transformation of plants with the aim of "antisense" inhibition of the expression of the sucrose transporter.

Transformation Agrobacteria were then used for infection of leaf segments of tobacco and potato.

In ten independently obtained transformands, in which the presence of the intact, non-rearranged chimeric gene was demonstrated by Southern blot analysis, changes in sucrose, hexose and starch content were respectively tested.

Figure 5:
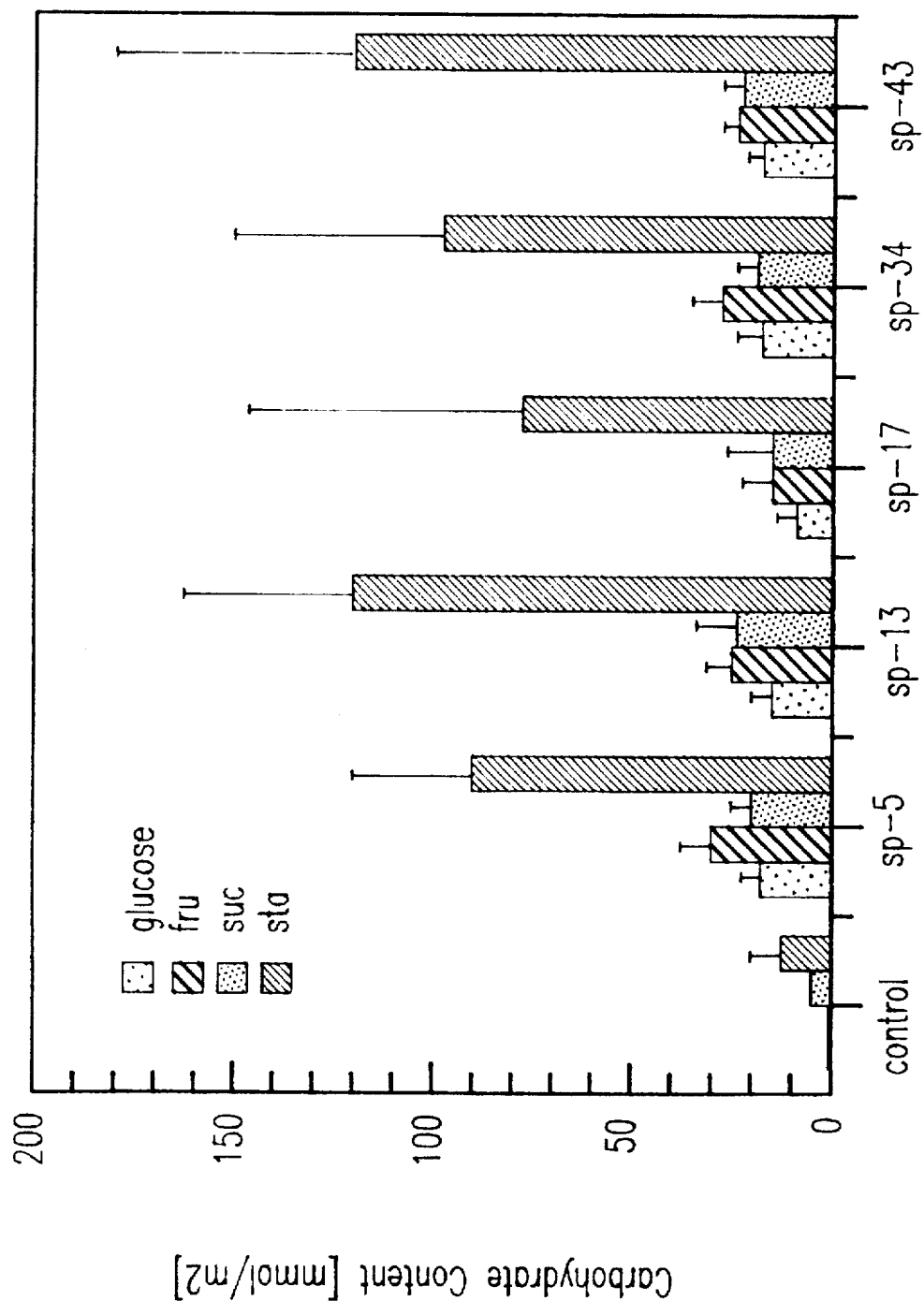
FIG. 5 is a graph of the content of various carbohydrates in the leaves of plants transformed with the plasmid BinAR-P62-anti.
Figure 6:
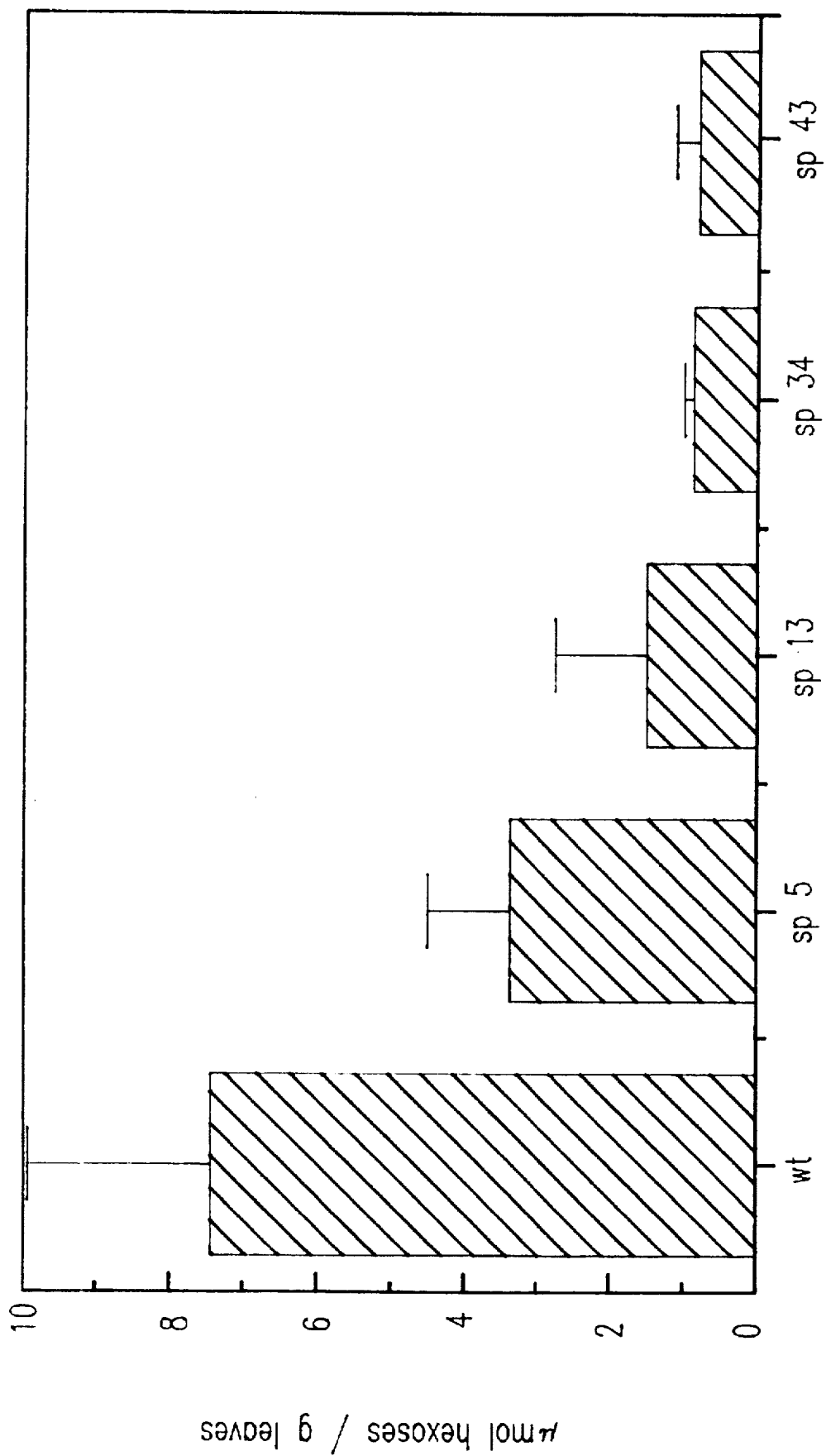
FIG. 6 is a graph of the efflux of carbohydrates from the petioles of plants transformed with the plasmid pBinAR-P62-anti.

Transformands, which contain the T-DNA from pBinAR-P62-anti, showed a strongly increased concentration of starches, hexoses and sucrose in the leaves (see FIG. 5). The efflux of carbohydrate from the petioles taken from the plants is greatly reduced in aqueous medium (see FIG. 6). From these data, the significance of the sucrose transporter for the transport away of the photoassimilate from the photosynthetically active organs is clearly seen. Since an inhibition of the activity of the transporter limits the transport away of carbohydrates, this results from a lowering of the transfer of photoassimilates to storage organs in the case of an over-expression, for example using the plasmid pBinAR-S21. Tobacco plants, in which the T-DNA from pBinAR-S21 has been integrated, show further a reduced apical dominance, i.e. they show a bushy growth. Such a phenotypical change is, for example very desirable in tomato plants. The plasmid pBinAR-S21 with the DNA sequence (Seq. ID No. 1) of the invention is therefore suited for the modification of plants with the purpose of improving important breeding characteristics such as bushy growth.

TABLE I

| Inhibitor | sucrose transport* (%) |
|---|---|
| Control | 100 |
| 0.5μM CCCP | 65 |
| 2.5μM CCCP | 21 |
| 25μM PCMBS | 73 |
| 100μM PCMBS | 21 |
| 25μM 2,4-DNP | 61 |
| 100μM 2,4-DNP | 9 |
| 1mM sodium arsenate | 34 |
| 10μM antimycin A | 59 |
| 1m cAMP | 102 |

CCCP = carbonyl cyanide m-chlorophenylhydrazone
PCMBS = p-chloromercuribenzenesulfonic acid
2,4-DNP = 2,4-dinitrophenol
* = in relation to Y Eplac 112 AINE-S21 (control)

TABLE II

| Competitor | sucrose transport* (%) |
|---|---|
| Control | 100 |
| 2mM sucrose | 28 |
| 2mM maltose | 58 |
| 10mM maltose | 37 |
| 2mM phenylglucoside | 7 |
| 2mM phloridzin | 16 |
| 2mM lactose | 91 |
| 10mM palatinose | 102 |
| 10mM trehalose | 103 |

* = in relation to YEplac 112 AINE - S21 (control)

We claim:

1. Plasmid pSK-S21 (DSM 7115).
2. Yeast strain YSH 2.64-1A-SUSY (DSM 7106).
3. Yeast strain YSH 2.64-1A-INV (DSM 7105).
4. A bacterium comprising a DNA fragment derived from a plant comprising the coding region of an oligosaccharide transporter gene derived from potato or spinach.
5. The bacterium according to claim 4, wherein said DNA fragment is selected from the group consisting of the coding region of SEQ ID No. 1 and the coding region of SEQ ID No. 3.
6. The bacterium according to claim 4, wherein said DNA fragment encodes an oligosaccharide transporter which comprises an amino acid sequence selected from the group consisting of SEQ ID No. 2 and SEQ ID No. 4.
7. A method of preparing bacterium with altered sucrose uptake ability, comprising the steps of transforming bacterium with a plasmid which comprises a DNA fragment derived from a plant comprising the coding region of an oligosaccharide transporter gene derived from potato or spinach.
8. The method according to claim 7, wherein said DNA fragment is selected from the group consisting of the coding region of SEQ ID No. 1 and the coding region of SEQ ID No. 3.
9. The method according to claim 7, wherein said DNA fragment encodes an oligosaccharide transporter which comprises an amino acid sequence selected from the group consisting of SEQ ID No. 2 and SEQ ID No. 4.
10. A method of altering the specificity of an oligosaccharide transporter, comprising the step of introducing a DNA fragment comprising the coding region of an oligosaccharide transporter gene derived from potato or spinach into a plasmid which is capable of recombination.
11. A composition comprising nucleic acid sequences comprising fragments of a DNA sequence derived from a plant comprising the coding region of an oligosaccharide transporter gene derived from potato or spinach, wherein said fragments of selectively hybridize to said DNA sequence, and wherein said fragments display the activity of an oligosaccharide transporter.
12. A method of isolating DNA sequences homologous to a DNA sequence which comprises the coding region of an oligosaccharide transporter gene derived from a plant, comprising the steps of:

preparing a probe comprising a DNA sequence which comprises the coding region of an oligosaccharide transporter gene derived from potato or spinach, a portion thereof or a complementary sequence thereto;

contacting said probe with a gene library; and identifying sequences within said gene library which hybridize to said probe.

13. A method of producing a transformed plant cell with a decreased synthesis of sucrose transporter relative to a non-transformed cell, comprising the steps of:

producing a DNA molecule comprising the following sequences:
  i) a promoter which is active in a plant or a plant cell;
  ii) at least one DNA fragment comprising the coding region of an oligosaccharide transporter gene that encodes a polypeptide as shown in SEQ ID NO: 2 or 4 wherein said DNA fragment is linked to said promoter in an antisense orientation; and incorporating said DNA molecule into the genome of a plant cell.

14. A recombinant expression vector comprising a DNA sequence which expresses a non-translatable RNA that inhibits formation of an oligosaccharide transporter in a transformed plant cell or transgenic plant, wherein the DNA sequence comprises the antisense sequence of a DNA encoding a polypeptide as shown in SEQ ID NO: 2 or 4.

15. A method of isolating DNA sequences encoding plant oligosaccharide transporters, comprising the steps of:

obtaining a first yeast strain with a suc2 gene that cannot be cleaved by invertase;

transforming said first yeast strain with a gene encoding sucrose synthase obtained from a plant cell thereby producing a second yeast strain which can cleave intracellular sucrose; and transforming said second yeast strain with a cDNA library in an expression vector for yeast cells, thereby isolating sequences encoding oligosaccharide transporters.

16. A yeast strain for identification of plant oligosaccharide transporters, obtainable by the process of claim 15.

17. A method of isolating sequences encoding oligosaccharide transporters comprising transforming a yeast strain selected from the group consisting of YSH 2.64-1A-SUSY and YSH 2.64-1A-INV with a cDNA library in an expression vector for yeast cells.

18. A method of inhibiting the expression of an oligosaccharide transporter gene, comprising the step of transforming a plant or a plant cell with plasmid pBin AR-P62-anti prepared from plasmid pSK-P62.

* * * * *